(12) United States Patent
Solomon

(10) Patent No.: US 8,651,862 B2
(45) Date of Patent: Feb. 18, 2014

(54) DENTAL TOOL WITH ADJUSTABLE HEAD

(76) Inventor: Jeffrey M. Solomon, Franklin, MI (US)

( * ) Notice: Subject to any disclaimer, the term of this patent is extended or adjusted under 35 U.S.C. 154(b) by 0 days.

(21) Appl. No.: 13/397,076

(22) Filed: Feb. 15, 2012

(65) Prior Publication Data

US 2012/0244486 A1  Sep. 27, 2012

Related U.S. Application Data

(60) Provisional application No. 61/466,224, filed on Mar. 22, 2011.

(51) Int. Cl.
*A61C 3/00* (2006.01)
(52) U.S. Cl.
USPC .......................................................... 433/147
(58) Field of Classification Search
USPC ................. 433/3, 30, 31, 141–147, 127–129; 132/308–311, 322–327; 600/189, 600/246–248
See application file for complete search history.

(56) References Cited

U.S. PATENT DOCUMENTS

| | | | | | |
|---|---|---|---|---|---|
| 470,211 | A | * | 3/1892 | Philips | 359/875 |
| 546,195 | A | * | 9/1895 | Sharp | 359/882 |
| 1,397,090 | A | * | 11/1921 | Dimas | 433/30 |
| 4,449,934 | A | * | 5/1984 | Salam | 433/143 |
| 4,731,896 | A | * | 3/1988 | de La Tour | 15/106 |
| 5,127,415 | A | * | 7/1992 | Preciutti | 132/323 |
| 5,394,584 | A | * | 3/1995 | Breitschmid | 15/167.1 |
| 5,458,486 | A | | 10/1995 | Ballard | |
| 5,741,132 | A | | 4/1998 | Usui et al. | |
| 6,666,682 | B1 | | 12/2003 | Meyerhof | |
| 2003/0091956 | A1 | * | 5/2003 | Chadwick et al. | 433/31 |
| 2005/0074719 | A1 | * | 4/2005 | Croop et al. | 433/30 |

* cited by examiner

*Primary Examiner* — Eric Rosen
(74) *Attorney, Agent, or Firm* — Harness, Dickey & Pierce, PLC

(57) ABSTRACT

A dental tool may include a head that may include a working portion and a neck. The neck may include a first end and a second end, and the working portion may extend from the first end. A handle may include a clamp and a socket. The socket may be configured to receive the second end of the neck. The second end may pivot within the socket to move the working portion and the neck relative to the handle. The clamp may be adapted to selectively fix the second end relative to the handle.

18 Claims, 10 Drawing Sheets

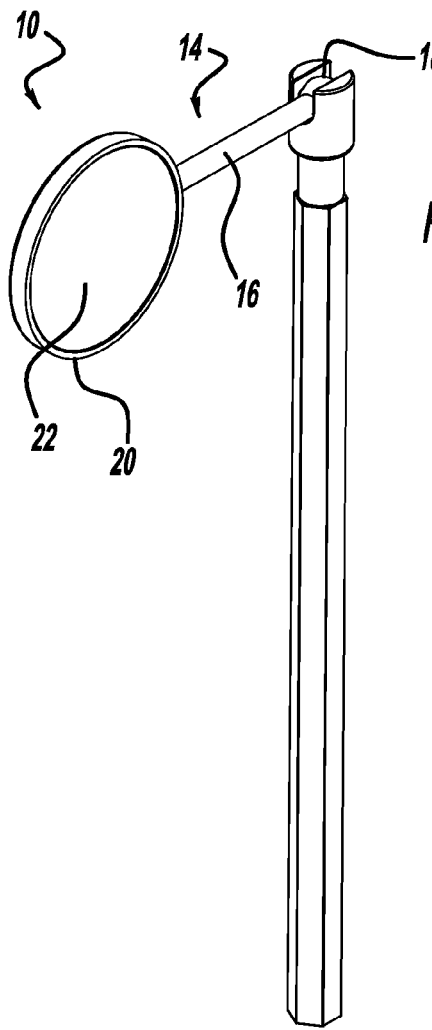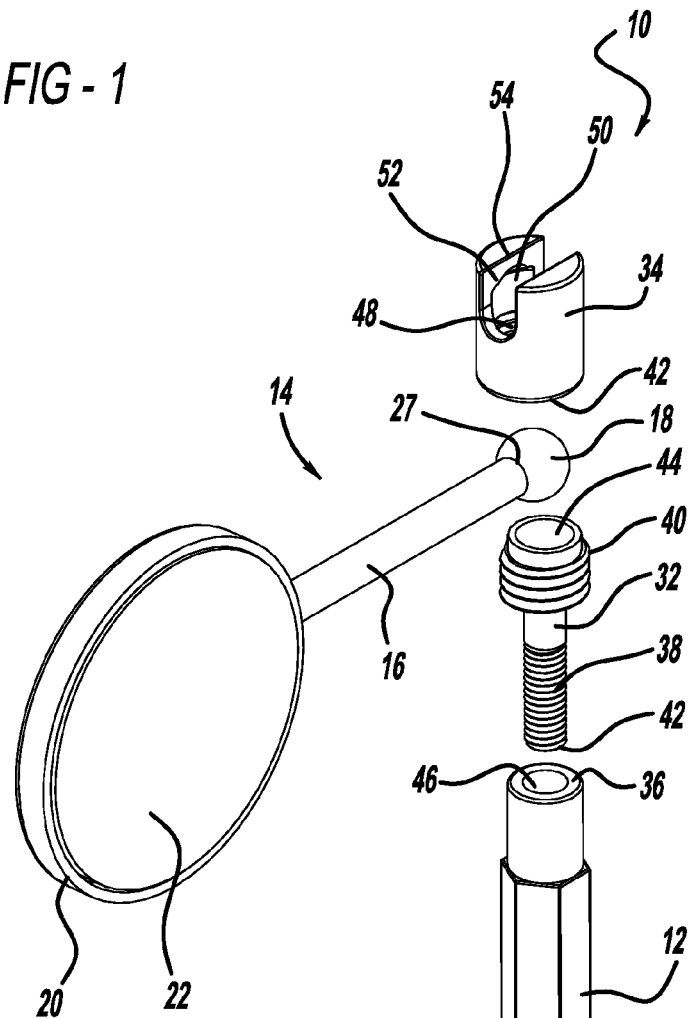
FIG-1
FIG-2

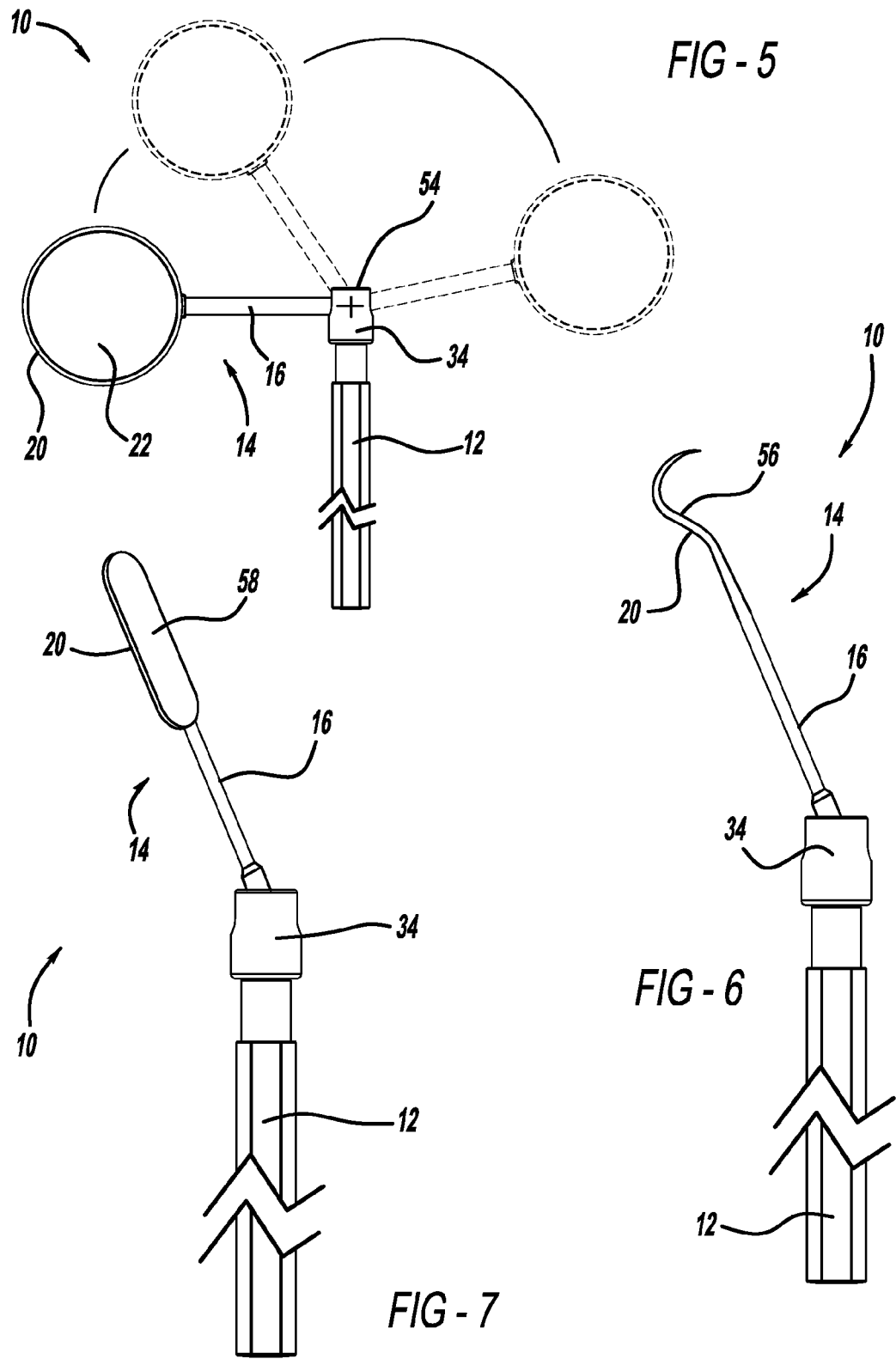

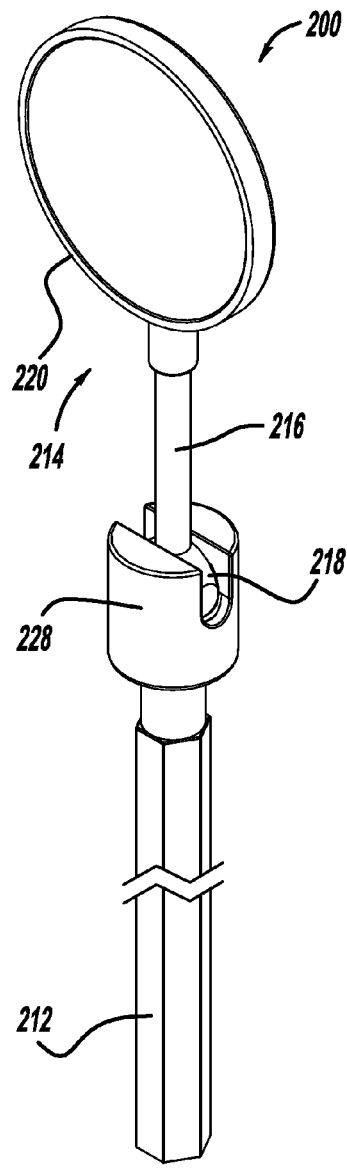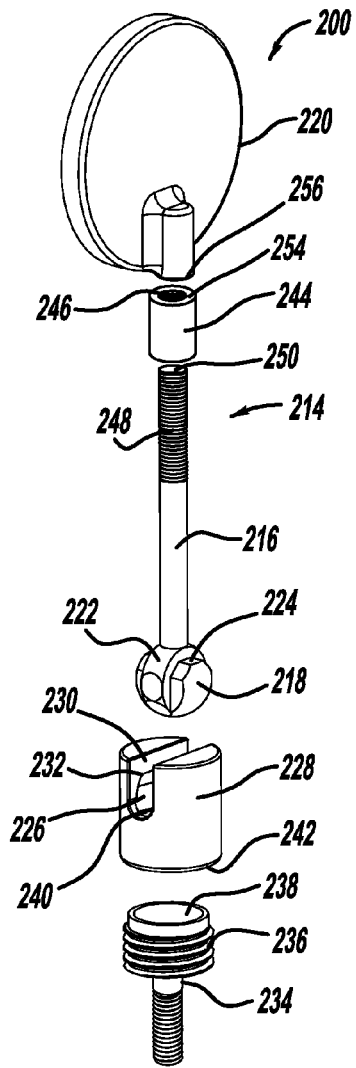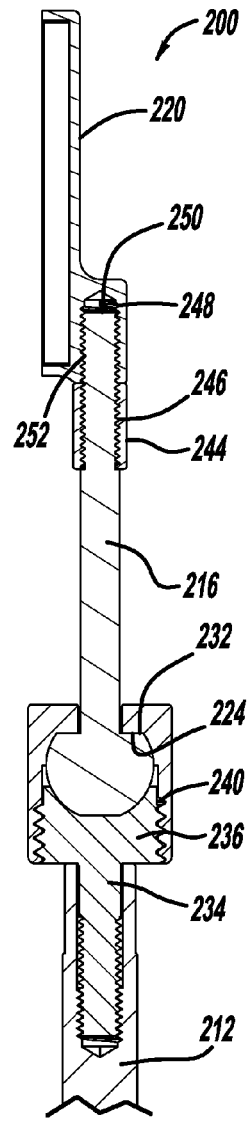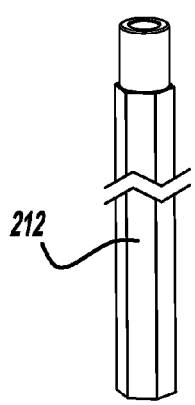
FIG - 10
FIG - 11
FIG - 12

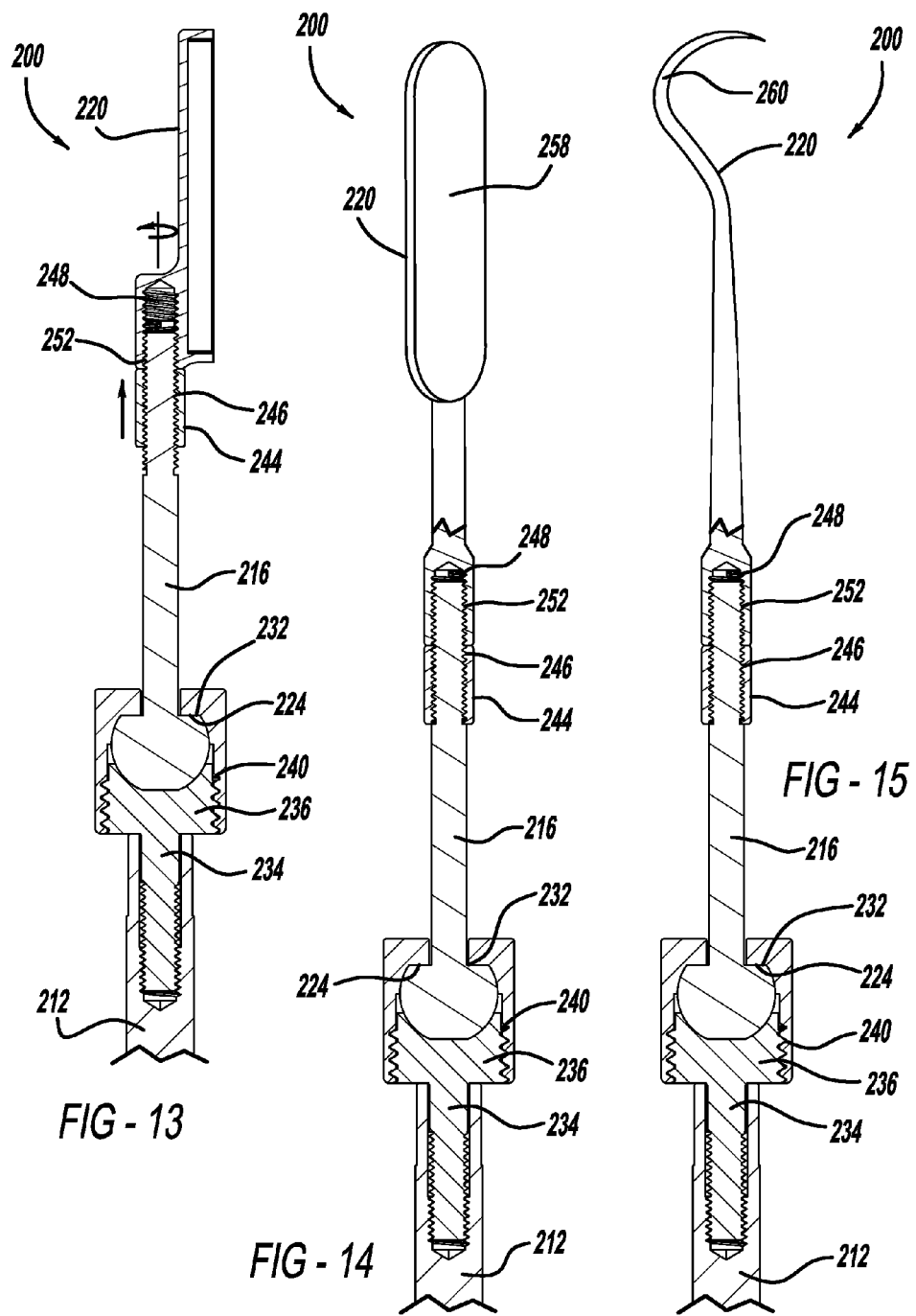

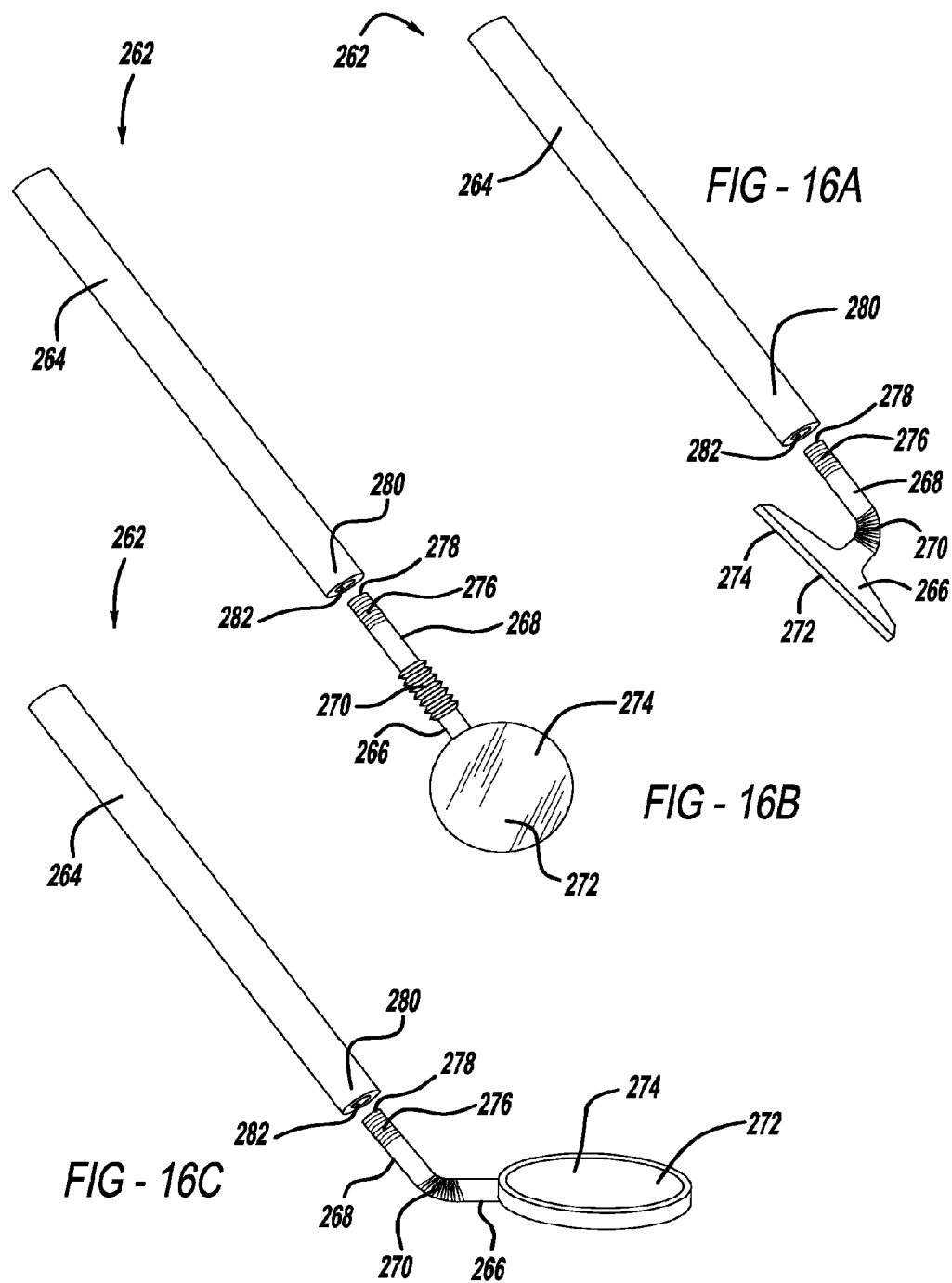

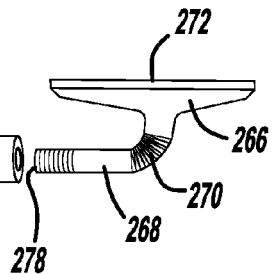
FIG - 17A
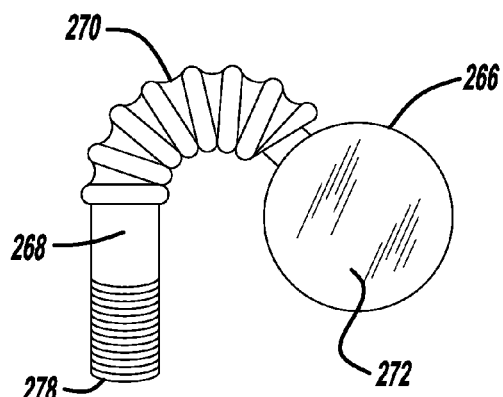
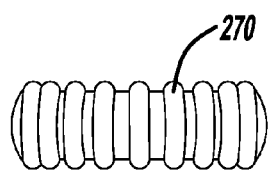
FIG - 17C
FIG - 17D
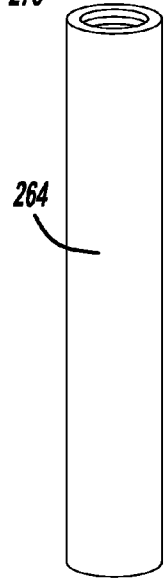
FIG - 17B
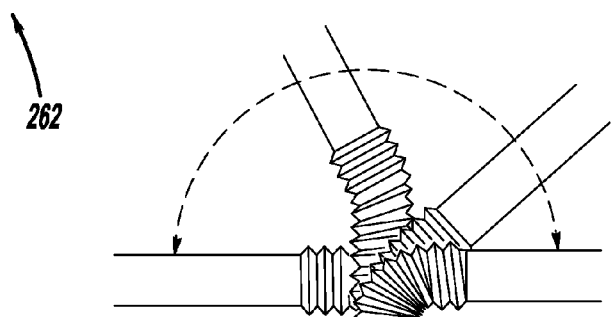
FIG - 17E

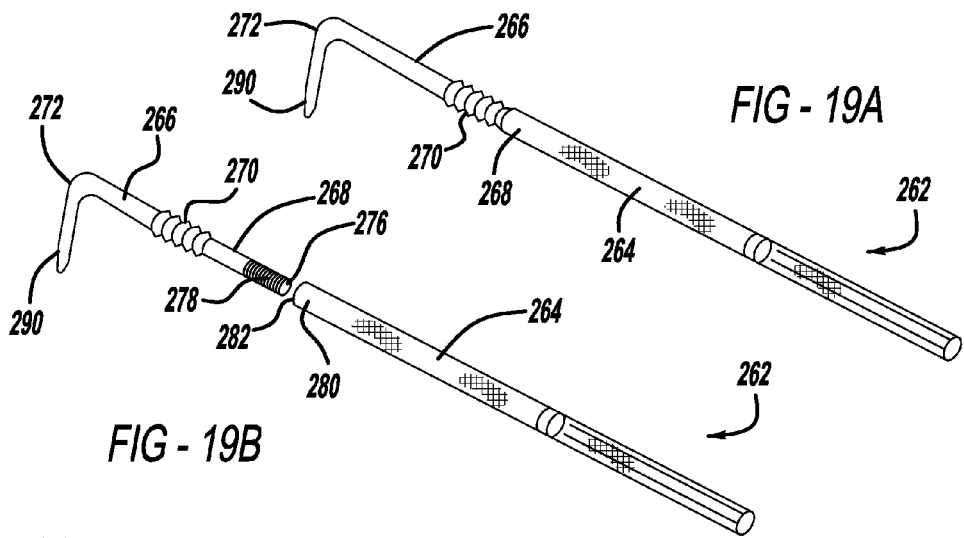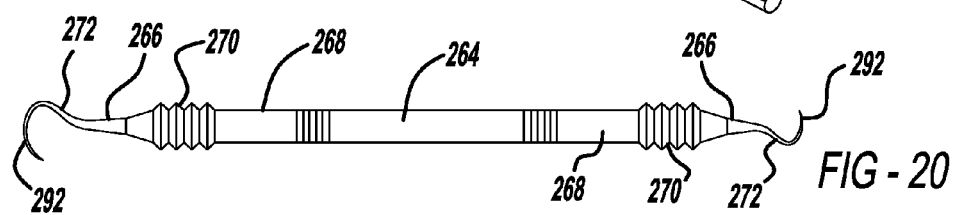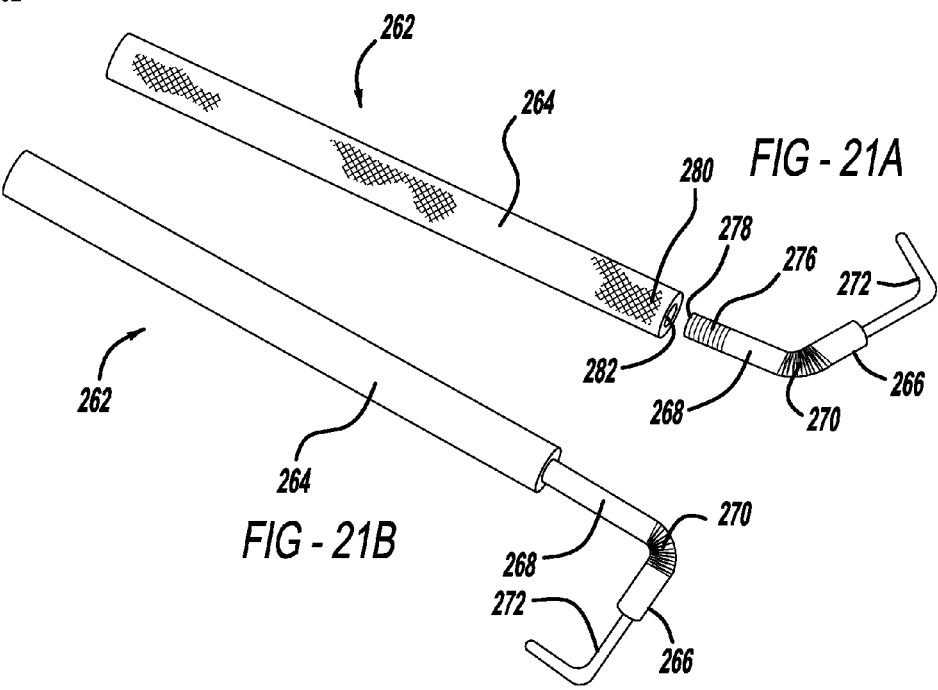

DENTAL TOOL WITH ADJUSTABLE HEAD

CROSS-REFERENCE TO RELATED APPLICATION

This application claims the benefit of U.S. Provisional Application No. 61/466,224, filed on Mar. 22, 2011. The entire disclosure of the above application is incorporated herein by reference.

FIELD OF THE INVENTION

This invention relates to adjustable dental tools and more particularly, to a novel apparatus where the head of the tool includes an accordion section which allows the tool to be bent and twisted for maximum adjustability.

BACKGROUND OF THE INVENTION

Often, a dentist's view and working environment in a patient's mouth is obstructed because of lack of adjustability of his dental mirror and/or instrument. A problem with current designs is that the adjustability, if any, is restricted to the location of the hinges or the orientation of the mirror and instrument.

SUMMARY OF THE INVENTION

The present invention contemplates an adjustable dental tool in which the working portion of the tool can be manipulated relative to the tool handle to position the head in a desirable configuration to carry out a task or to provide a better viewing angle within a patient's mouth. In one form, the present disclosure provides a dental tool that may include a head and a handle. The head may include a working portion and a neck. The neck may include a first end and a second end, and the working portion may extend from the first end. The handle may include a clamp and a socket. The socket may be configured to receive the second end of the neck. The second end may pivot within the socket to move the working portion and the neck relative to the handle. The clamp may be adapted to selectively fix the second end relative to the handle.

In another form, the present disclosure provides a dental tool that may include a working portion and a neck. The neck may include a proximal end and a distal end. The working portion is coupled to the distal end of the neck. A sleeve couples to the distal end of the neck and is movable between a first position allowing the working portion to rotate relative to the neck and a second position restricting rotation of the working portion relative to the neck.

In another form, the present disclosure provides a dental tool that may include a working portion and a neck. The neck may include a proximal end, a distal end and a first longitudinal axis extending between the proximal and distal ends. The working portion may be coupled to the distal end of the neck. A handle may include a first end, a second end and a second longitudinal axis extending between the first and second ends. The first end may be coupled to the proximal end of the neck, and the neck may be movable relative to the handle between a first position in which the first and second longitudinal axes are substantially collinear and a second position in which the first longitudinal axis is angled relative to the second longitudinal axis.

The design offers the advantages of allowing different dental heads to be used with the same handle which will allow the tool to be sold in kits, thereby reducing the cost of the tool since only a single handle is needed for a multitude of dental heads. Further, the handle can include a single coupling portion on its proximal end for attachment of a single dental head, or it can include a plurality of coupling portions on both ends for attachment of a plurality of dental heads.

The design offers an additional advantage of maximum adjustability of the dental head. The adjustable portion of the neck of the dental head provides for pivoting movement of the dental head relative to the proximal end of the dental head and radial twisting movement of the dental head relative to the longitudinal axis of the neck. The adjustable dental tool provides the dentist with the capability to adjust the dental head to a multitude of positions for optimal viewing or operation within a patient's mouth.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 shows a perspective view of the adjustable dental tool with a pivoting neck, threaded mirror head and handle, wherein the mirror head is positioned at a 90° angle relative to the handle;

FIG. 2 shows an exploded view of the adjustable dental tool with the mirror head positioned at the 90° angle relative to the handle;

FIG. 5 shows a perspective view of the range of motion of the pivoting section of the neck of the dental tool;

FIG. 6 shows a perspective view of a second embodiment of the head of the the dental tool;

FIG. 7 shows a perspective view of a third embodiment of the head of the dental tool;

FIG. 10 shows a perspective view of a sixth embodiment of the adjustable dental tool with the pivoting neck, threaded mirror head and handle, wherein the mirror head is positioned at a 0° angle relative to the handle;

FIG. 11 shows an exploded view of the sixth embodiment of the adjustable dental tool with the mirror head positioned at the 0° angle relative to the handle;

FIG. 12 shows a section view of the sixth embodiment of the dental tool with the mirror head positioned at the 0° angle relative to the handle;

FIG. 13 shows a section view of the twistable function of the mirror head relative to the neck of the tool;

FIG. 14 shows a section view of a seventh embodiment of the head of the dental tool; and FIG. 15 shows a section view of an eighth embodiment of the head of the dental tool.

FIGS. 16A-C show various perspective views of the adjustable dental tool with a bendable, threaded, mirror head and handle;

FIGS. 17A-C show various perspective views of the bendable section of the neck of the tool;

FIG. 17D shows a perspective view of the twistable function of the bendable section of the neck of the tool;

FIG. 17E shows a perspective view of the range of motion of the bendable section of the neck of the tool;

FIGS. 19A-B show perspective views of a fourth and fifth embodiment of the dental tool;

FIG. 20 shows a perspective view of a sixth embodiment of the dental tool; and

FIGS. 21A-B show perspective views of a seventh embodiment of the dental tool.

DETAILED DESCRIPTION OF THE PREFERRED EMBODIMENTS

Figure 3:
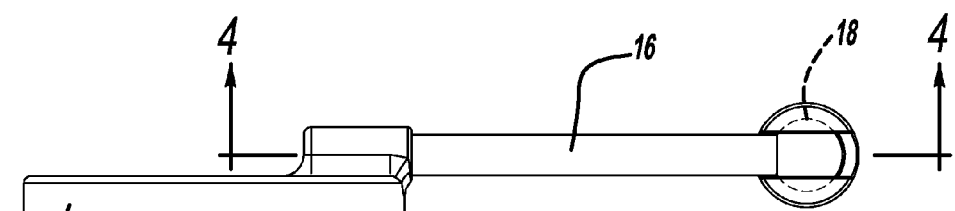
FIG. 3 shows a top view of the pivoted neck and mirror head of FIG. 1.
Figure 4:
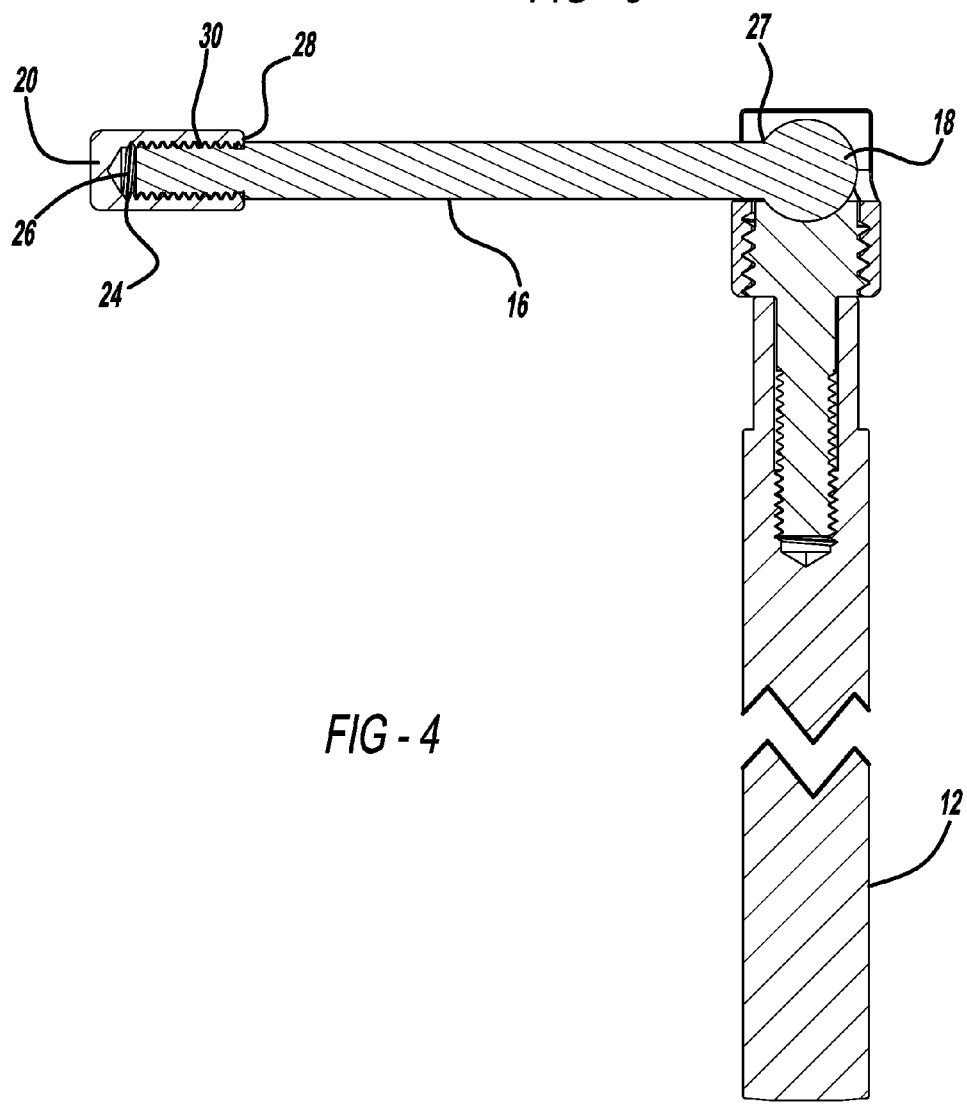
FIG. 4 shows a section view of the assembled dental tool with the mirror head positioned at the 90° angle relative to the handle.

The following description of the preferred embodiment(s) is merely exemplary in nature and is in no way intended to limit the invention, its application, or uses.

FIGS. 1-15 illustrate various views of an adjustable dental tool 10 including a handle 12 and a head 14 that can be placed in a patient's mouth. Referring to FIGS. 1-5, the head 14 includes a neck 16 having a distal end 26 and a proximal end 27. The neck further includes a ball 18 located on the proximal end 27 of the neck 16 and a working portion 20 on the distal end 26 of the neck 16, which is in the form of a mirror 22 according to this embodiment. As will be discussed in greater detail below, the ball 18 can be pivoted to affix the head 14 and ultimately the working portion 20, e.g. the mirror 22, in a desired position. The head 14 additionally includes a male coupling portion 24 or female coupling portion on the distal end 26 of the neck, which is a male threaded portion 24 in this embodiment. The proximal end 28 of the working portion 20 includes a complementary female coupling portion 30 or male coupling portion, which is a female threaded portion 30 in this embodiment that is in engagement with the coupling portion 24 of the neck 16.

Referring specifically to FIG. 2, the handle 12 includes a clamp 32 and a socket 34 coupled to a distal end 36 of the handle 12 for attaching the head 14 to the handle 12 and adjusting the neck 16 to a desired angle relative to the longitudinal axis of the handle 12. The clamp 32 includes a male coupling portion 38, 40 or female coupling portion on both its proximal 42 and distal 44 ends, which is a male threaded portion 38, 40 in this embodiment. The distal end 36 of the handle 12 and a proximal end 42 of the socket 34 both include complementary female coupling portions 46, 48 or male coupling portions, which are female threaded portions 46, 48 in this embodiment that are in engagement with the coupling portions 38, 40 of the clamp 32.

The socket 34 further includes a receptacle 50 for receiving the ball 18 on the head 14 of the adjustable dental tool 10. As discussed in greater detail below, the ball 18 fits within the receptacle 50 so that the neck 16 exits through a slot 52 located in a distal end 54 of the socket 34. The slot 52 allows the neck 16 to pivot in a range of 0° to 90° from the longitudinal axis of the handle 12, in conjunction with the ball 18 as the ball 18 is rotated within the receptacle 50, altering the position of the working portion 20 relative to the distal end 54 of the socket 34 (further demonstrated in FIG. 5). Further, the ball 18 may be twisted in a range of 0° to 360° both clockwise and counterclockwise in the radial direction along the longitudinal axis of the handle 12, altering the position of the working portion 20 relative to the axis running the length of the handle 14. The neck 16 may also be rotated and twisted simultaneously. The coupling of the clamp 32 and the socket 34 may be tightened such that the distal end 44 of the clamp 32 contacts the ball 18 and increases a compressive force on the ball 18 from the clamp 32 and the walls of the receptacle 50. The application of the compressive force will cause the ball 18 to remain in its set position thereby temporarily fixing the position of the working portion 20.

As Illustrated in FIGS. 6 and 7, the adjustable dental tool 10 may include a variety of working portions 20. Specifically, FIG. 6 is a perspective view of an embodiment of the adjustable dental tool 10 including the working portion 20 illustrated as a pick head 56. This embodiment includes the same remaining elements of the adjustable dental tool 10 illustrated in FIGS. 1-5. Specifically, FIG. 7 is a perspective view of one other embodiment of the adjustable dental tool 10 including the working portion 20 that is illustrated as a cement spatula head 58. This embodiment also contains the same remaining elements of the adjustable dental tool 10 illustrated in FIGS. 1-5.

Figure 8:
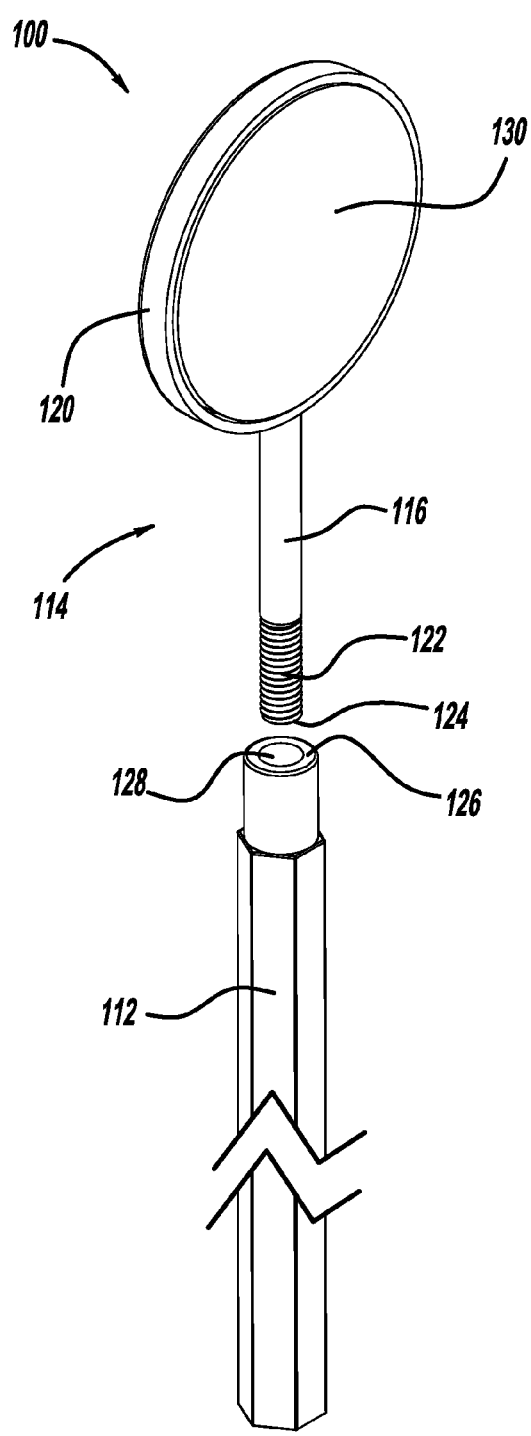
FIG. 8 shows a perspective view of a fourth embodiment of the dental tool.
Figure 9:
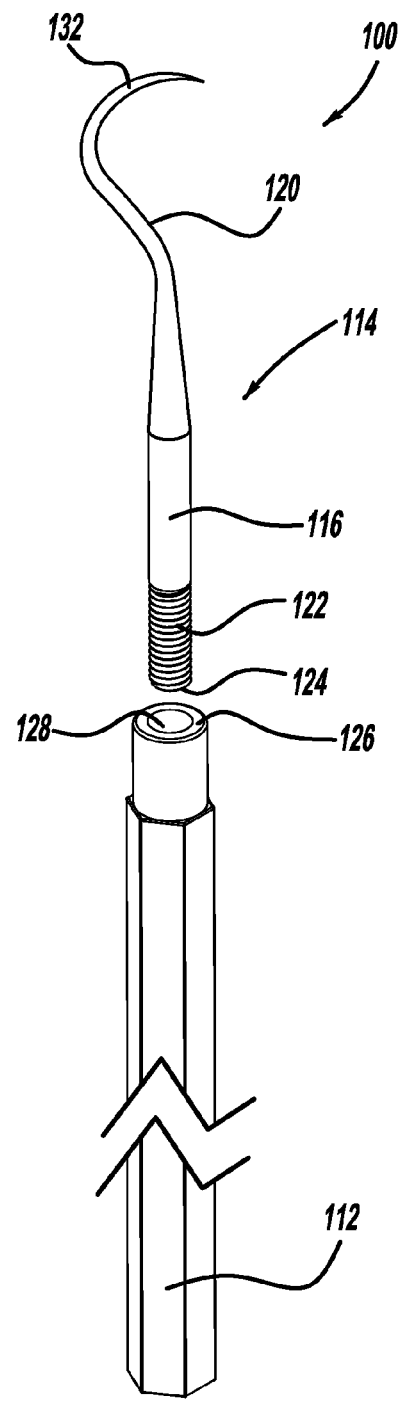
FIG. 9 shows a perspective view of a fifth embodiment of the dental tool.
Figure 18A:
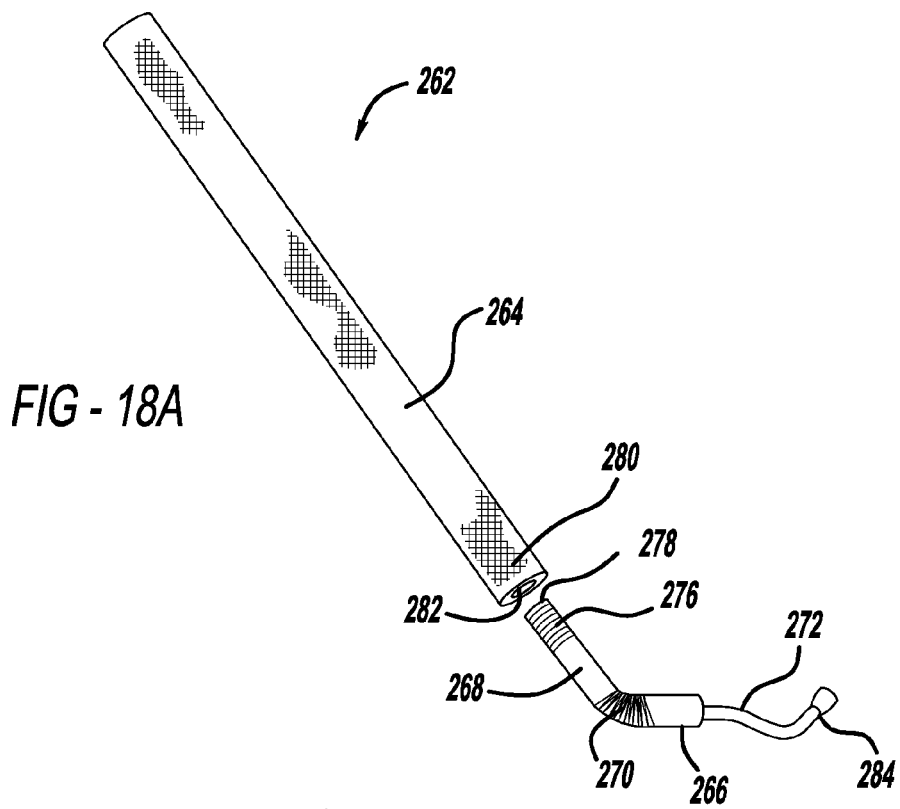
FIGS. 18A-C show perspective views of three different embodiments of the head of the dental tool.
Figure 18B:
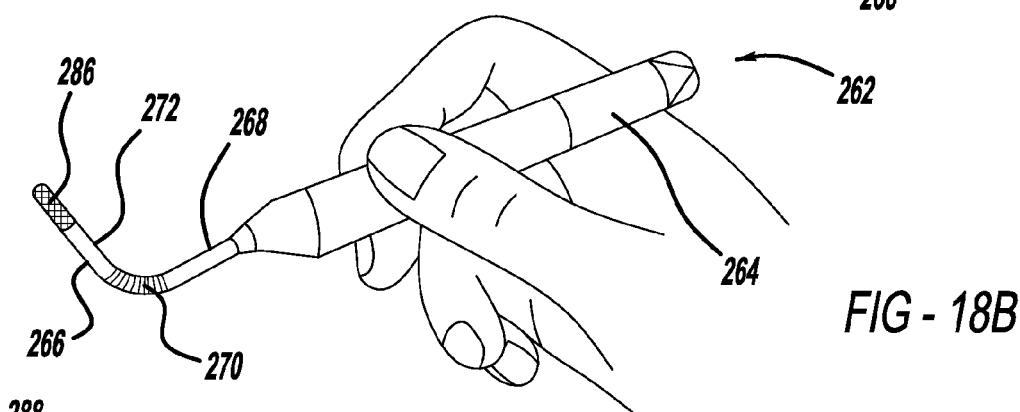
Figure 18C:
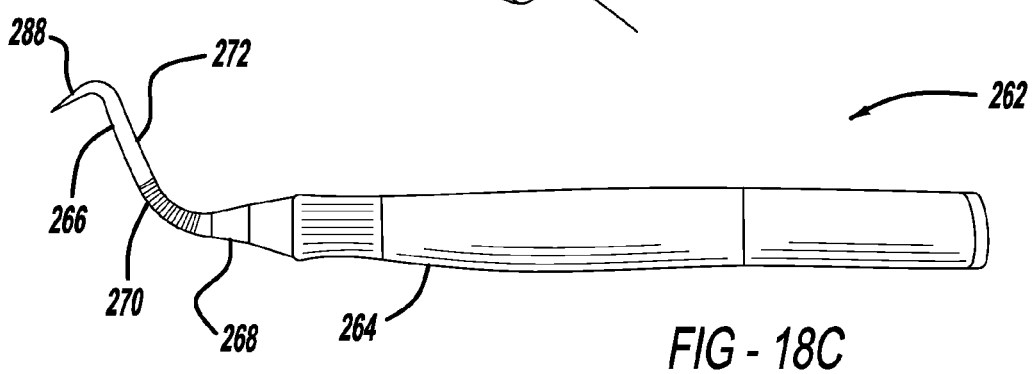

FIGS. 8-9 illustrate embodiments of a dental tool 100 including a handle 112, a head 114, a neck 116, and a working portion 120 wherein the neck 116 is fixed at a predetermined angle from the longitudinal axis of the handle 112 (for example only, 0°). The neck 116 includes a male coupling portion 122 or female coupling portion on a proximal end 124 of the neck 116, which is a male threaded portion 122 in this embodiment. A distal end 126 of the handle 112 includes a complementary female coupling portion 128 or male coupling portion, which is a female threaded portion 128 in this embodiment that is in engagement with the coupling portion 122 of the neck 116. The dental tool 100 may include a variety of different, interchangeable, working portions. The working portion 120 of the embodiment shown here is a mirror 130. Specifically, FIG. 9 is a perspective view of another embodiment of the dental tool 100 including the working portion 120 that is illustrated as a pick head 132. This embodiment also contains the same remaining elements of the dental tool 100 illustrated in FIG. 8.

Referring specifically to FIGS. 10-13, an adjustable dental tool 200 includes all of the elements of the adjustable dental tool illustrated in FIGS. 1-7 and further illustrates an embodiment of the adjustable dental tool 200 where the rotational position of a ball 218 can be temporarily fixed in a range of 0° to 90° from the longitudinal axis of a handle 212, and the radial position of the ball 218 relative to the axis running the length of the handle 212 is fixed. The ball 218 includes a raised portion 222 and a plurality of flat portions 224. The raised portion 222 protrudes out of a receptacle 226 of a socket 228 and rests within a slot 230, fixing the radial position of the ball 218. The plurality of flat portions 224 engage with a complementary flat portion 232 of the receptacle, stopping the rotation of the ball at predetermined stop angles in the range of 0° to 90° from the longitudinal axis of the handle. A clamp 234, including a male coupling portion 236 or female coupling portion on a distal 238 end of the clamp 234 that engages with a complementary male or female coupling portion 240 on a proximal 242 end of the socket 228, may then be engaged to apply compressive pressure to the ball 218, temporarily fixing the ball 218, in the desired angle.

Further, the adjustable dental tool 200 includes a sleeve 244 for adjusting the position of a working portion 220 relative to the axis running the length of the handle 212. The sleeve 244 includes a male or female coupling portion 246, which is a female threaded portion 246 in this embodiment. The coupling portion 246 on the sleeve 244 is engaged with a complementary male coupling portion 248 or female coupling portion on a distal end 250 of a neck 216, which is a male threaded portion 248 in this embodiment. The sleeve may be threaded onto the distal end 250 of the neck 216 and provide a stop position for the working portion 220. The working portion 220 includes a similar coupling portion 252 to the coupling portion 246 of the sleeve 244, which is a female threaded portion 252 in this embodiment, and the coupling portion 252 of the working portion 220 is threaded onto the distal end 250 of the neck 216 and contacts a distal end 254 of the sleeve 244. FIGS. 10-12 show the raised portion 222 having opposed flat surfaces and a rounded surface, the opposed flat surfaces being substantially parallel to each other, a plurality of the flat surfaces 224 extending perpendicularly from the raised portion 222.

As illustrated in FIG. 13, the position of the sleeve 244 defines the radial position of the working tool 220 and allows the working tool 220 to be twisted in a range of 0° to 360° both clockwise and counterclockwise in the radial direction along the longitudinal axis of the handle 212, altering the position of the working portion 220 relative to the axis running the length of the handle 212. Once the user determines the desired radial position of the working tool 220, the sleeve 244 is turned counterclockwise until the distal end 254 of the sleeve 244 contacts a proximal end 256 of the working tool 220, preventing the working tool 220 from being threaded further onto the neck 216. The radial position of the working portion 220 is temporarily fixed until a new desired radial position is set.

As Illustrated in FIGS. 14 and 15, the adjustable dental tool 200 may include a variety of working portions 220. Specifically, FIG. 14 is a perspective view of an embodiment of the adjustable dental tool 200 including the working portion 220 illustrated as a cement spatula head 258. This embodiment includes the same remaining elements of the adjustable dental tool 200 illustrated in FIGS. 10-13. Specifically, FIG. 15 is a perspective view of one other embodiment of the adjustable dental tool 200 including the working portion 220 that is illustrated as a pick head 260. This embodiment also contains the same remaining elements of the adjustable dental tool 200 illustrated in FIGS. 10-13.

The scope of this disclosure may include embodiments including working portions 20 that may be both detachably connected to the neck 16 and may be irremovably connected to the neck 16. This embodiment is not limited to the mirrors 22 shown in these illustrations but could include any working portions 20.

It is envisioned that the adjustable dental tool may be assembled as a kit including a single or plurality of handles 12 and a plurality of removable working portions 20 that can all be interchanged on the handle 12. Each handle 12 may include a single complementary coupling portion 46 that is in engagement with the female or male coupling portion 38 of the clamp 32 or may include a plurality of complementary coupling portions 46 located on both ends of the handle 12 for engagement with a plurality of male coupling portions 38 or female coupling portions of a plurality of clamps 32.

The handle 12, neck 16 and working portions 20 and, in particular, the ball 18 and socket 34, should be made from a material that is fully autoclavable for sterilization purposes.

Working portions 20 are not limited to the working portions 20 illustrated in the embodiments of the Figures. Additional working portions may include, but are not limited to, a flosser, explorers, periodontal probes, saliva ejectors, gauges, cheek retractors, ligature directors, band pushers, scalers, bracket placers, periodontal curettes, periosteal elevators, filling instruments, root tip instruments, waxing instruments, burnishers, carvers, cavity liners, cement spatulas, cleoid discoids, and excavators, by way of non-limiting example.

Several benefits and advantages of the present invention over prior dental tools include adjustment capabilities of the head 14 relative to the handle 12, and the orientation of the working portion 20 of the head 14 itself. An additional advantage is the uniform handle 12 that may receive a plurality of dental heads 14 allowing for the formation of kits including a plurality of handles 12 and dental heads 14 that are all interchangeable.

FIGS. 16-21 illustrate various views of an adjustable dental tool 262 including a handle 264 and a head 266 that can be placed in a patient's mouth. Referring specifically to FIGS. 16A-C, the head 266 includes a neck 268 having an adjustable section 270 and a working portion 272 which is in the form of a mirror 274 according to this embodiment. As will be discussed in greater detail below, the adjustable section 270 can be bent and/or twisted to affix the head 266 and ultimately the working portion 272, e.g. the mirror 274, in a desired position. The head 266 additionally includes a male coupling portion 276 or female coupling portion on its proximal end 278, which is a male threaded portion 276 in this embodiment. The distal end 280 of the handle 264 includes a complementary female coupling portion 282 or male coupling portion, which is a female threaded portion 282 in this embodiment that is in engagement with the coupling portion 276 of the head 266.

Referring specifically to FIGS. 17A-E, the neck 268 includes an adjustable section 270 that may be manipulated to adjust the position of the working portion 272 relative to the proximal end 278 of the head 266. The adjustable section 270 may be of an accordion construction to allow bending capability anywhere along its length. FIGS. 17B, 17C, and 17E demonstrate the bending capabilities of the adjustable section 270 which may be bent in a range of 0° to 360° from the longitudinal axis of the handle 264 in all directions, altering the position of the working portion 272 relative to the proximal end 278 of the head 266. FIG. 17D demonstrates the twisting capabilities of the adjustable section 270 which allows the head 266 to be turned in a range of 0° to 360° both clockwise and counterclockwise in the radial direction along the longitudinal axis of the handle 264, altering the position of the working portion 272 relative to the axis running the length of the handle 264. The adjustable section 270 may also be bent and twisted simultaneously. The material of the adjustable section 270 is rigid enough to withstand forces encountered in the oral cavity without distortion, but also is flexible enough for the operator to manipulate the head 266 to the desired angle with ease.

As Illustrated in FIGS. 18-21, the adjustable dental tool 262 may include a variety of working portions 272. Specifically, FIG. 18A is a perspective view of an embodiment of the adjustable dental tool 262 including a working portion 272 illustrated as an excavator 284. This embodiment includes the same remaining elements of the adjustable dental tool 262 illustrated in FIGS. 16A-C. Specifically, FIGS. 18B and 3C are perspective views of two other embodiments of the adjustable dental tool 262 including working portions 272 that are illustrated as a filling head 286 and a probe head 288, respectively. Each of these embodiments also contain the same remaining elements of the adjustable dental tool 262 illustrated in FIGS. 16A-C.

FIG. 19A illustrates an embodiment of the adjustable dental tool 262 including a handle 264, a head 266, and a neck 268 having an adjustable section 270 wherein the head 266 is irremovably attached to the handle 264. The working portion 272 of the embodiment shown here is a root elevator 290. Further, as seen in FIG. 19B, the adjustable dental tool 262 may have the same embodiment as in FIG. 19A with the same working portion 272, except include a removable head 266 as in FIGS. 16A-C. The adjustable section 270 of the head 266 is included in both the embodiment with the removable head 266 and the embodiment wherein the head 266 is irremovably attached to the handle 264.

FIG. 20 includes all of the elements of the adjustable dental tool illustrated in FIGS. 16A-C and further illustrates an embodiment of the adjustable dental tool 262 where two working portions 272, which in this embodiment are pick heads 292, may be connected to a single handle 264, one working portion 272 connected to each of the distal and proximal ends. The scope of this disclosure may include embodiments including working portions 272 that may be both detachably connected to the handle 264 and may be irremovably connected to the handle 264. This embodiment is not limited to the pick heads 292 shown in this illustration but could include any two working portions 272 in any combination.

It is envisioned that the adjustable dental tool may be assembled as a kit including a single or plurality of handles 264 and a plurality of removable working portions 272 that can all be interchanged on a handle 264. Each handle 264 may include a single complementary coupling portion 282 that is in engagement with the female or male coupling portion 276 of the working portion 272 or may include a plurality of complementary coupling portions 282 located on both ends of the handle 264 for engagement with a plurality of male or female coupling portions 276 of a plurality of working portions 272.

The handle 264 and working portions 272 and in particular the adjustable section 270 of the neck 268, should be made from a material that is fully autoclavable for sterilization purposes.

Working portions are not limited to the working portions illustrated in the embodiments of the Figures. Additional working portions may include, but are not limited to, a flosser, explorers, periodontal probes, saliva ejectors, gauges, cheek retractors, ligature directors, band pushers, scalers, bracket placers, periodontal curettes, periosteal elevators, filling instruments, root tip instruments, waxing instruments, burnishers, carvers, cavity liners, cement spatulas, cleoid discoids, and excavators, by way of non-limiting example.

Several benefits and advantages of the present invention over prior dental tools include adjustment capabilities of the head 266 in any of the angle of the neck 268, the location of the bend in the neck 268, and the orientation of the working portion 272 of the head 266 itself. An additional advantage is the uniform handle 264 that may receive a plurality of dental heads 266 allowing for the formation of kits including a plurality of handles 264 and dental heads 266 that are all interchangeable.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A dental tool comprising:
a head including a working portion and a neck, said neck including a first end and a second end, said working portion extending from said first end; and
a handle including a clamp and a socket, said socket being configured to receive the second end of said neck, wherein the second end pivots within the socket to move the working portion and the neck relative to the handle, wherein the clamp is threadably received within said socket and is adapted to selectively fix the second end relative to the handle,
wherein the second end includes a ball that is pivotable within the socket to move the neck relative to the handle, the ball having a raised portion and a plurality of flat surfaces, the raised portion including opposed flat surfaces and a rounded surface, the raised portion protruding out of a receptacle formed in the socket and into a slot formed in the socket, the opposed flat surfaces being substantially parallel to each other, and the plurality of flat surfaces selectively mating with corresponding flat surfaces formed on said socket to position the neck at one of a plurality of predetermined angles relative to a longitudinal axis of the handle.

2. The dental tool of claim 1, further comprising a sleeve coupling to the first end of the neck, wherein said sleeve is movable between a first position allowing the working portion to rotate relative to the neck and a second position restricting rotation of the working portion relative to the neck.

3. The dental tool of claim 2, wherein said sleeve includes a first threaded portion coupling with a second threaded portion of the neck, said sleeve being threadably movable relative to the neck between the first and second positions, whereby the neck applies a force on the working portion and fixes the rotational position of the working portion when the sleeve is in the second position.

4. The dental tool of claim 1, wherein the socket and the second end cooperate to restrict movement of the second end to pivoting within a single plane.

5. The dental tool of claim 1, wherein said clamp is movable between a first position allowing the movement of the second end relative to the socket and a second position restricting movement of the second end relative to the socket.

6. The dental tool of claim 1, wherein said clamp is removably attached to an end of said handle.

7. The dental tool of claim 1, wherein said working portion includes at least one of a mirror, a pick, a flosser, an explorer, a periodontal probe, a saliva ejector, a gauge, a cheek retractor, a ligature director, a band pusher, a scaler, a bracket placer, a periodontal curette, a periosteal elevator, a filling instrument, a root tip instrument, a waxing instrument, a burnisher, a carver, a cavity liner, a cement spatula, a cleoid discoid, and an excavator.

8. The dental tool of claim 1, wherein the neck and the working portion include a fully autoclavable material.

9. The dental tool of claim 1, wherein the ball directly pivotably engages both of the clamp and the socket.

10. A dental tool comprising:
a working portion;
a neck including a proximal end and a distal end, said working portion being coupled to the distal end of the neck;
a sleeve coupling to the distal end of the neck, wherein said sleeve is movable between a first position allowing the working portion to rotate relative to the neck and the sleeve about a first axis and a second position restricting rotation of the working portion relative to the neck and the sleeve; and
a handle including a socket and a clamp, the socket pivotably engaged with a ball formed on the proximal end of the neck to allow the neck to pivot relative to the handle about a second axis, the ball including an annularly extending raised portion and a plurality of flat surfaces extending perpendicularly from the raised portion, wherein the clamp is threadably received within said socket and is adapted to selectively fix the proximal end relative to the handle, the raised portion comprising opposed flat surfaces substantially parallel to each other and a rounded surface, and wherein the raised portion protrudes out of a receptacle formed in the socket and into a slot formed in the socket.

11. The dental tool of claim 10, wherein said working portion includes a first threaded portion coupling with a second threaded portion of the neck, said working portion being threadably movable relative to the neck among a plurality of rotational positions.

12. The dental tool of claim 11, wherein said sleeve includes a third threaded portion coupling with the second threaded portion of the neck, said sleeve being threadably movable to the second position to apply a force on the working portion to restrict movement of the working portion relative to the neck.

13. The dental tool of claim 10, wherein the socket and the proximal end cooperate to restrict movement of the proximal end to pivoting within a single plane.

14. The dental tool of claim 10, wherein said clamp includes a first threaded portion coupling with a second threaded portion surrounding the socket, said clamp being threadably movable relative to a threaded portion of the handle to a position in which the clamp restricts movement of the proximal end relative to the socket.

15. The dental tool of claim 10, wherein the handle is removably fixed to the neck.

16. The dental tool of claim 10, wherein said working portion includes at least one of a mirror, a pick, a flosser, an explorer, a periodontal probe, a saliva ejector, a gauge, a cheek retractor, a ligature director, a band pusher, a scaler, a bracket placer, a periodontal curette, a periosteal elevator, a filling instrument, a root tip instrument, a waxing instrument, a burnisher, a carver, a cavity liner, a cement spatula, a cleoid discoid, and an excavator.

17. The dental tool of claim 10, wherein the neck and the working portion include a fully autoclavable material.

18. The dental tool of claim 10, wherein the ball directly pivotably engages both of the clamp and the socket.

* * * * *